US00PP16963P2

(12) United States Plant Patent
Smith

(10) Patent No.: US PP16,963 P2
(45) Date of Patent: Aug. 8, 2006

(54) ***CHRYSANTHEMUM* PLANT NAMED 'YOFIONA'**

(50) Latin Name: *Chrysanthemum×morifolium*
Varietal Denomination: Yofiona

(75) Inventor: Mark A. Smith, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 11/212,385

(22) Filed: Aug. 26, 2005

(51) Int. Cl.
*A01H 5/00* (2006.01)

(52) U.S. Cl. ..... Plt./296

(58) Field of Classification Search ..... Plt./296
See application file for complete search history.

*Primary Examiner*—Anne Marie Grunberg
*Assistant Examiner*—Georgia Helmer
(74) *Attorney, Agent, or Firm*—C. A. Whealy

(57) ABSTRACT

A new and distinct cultivar of *Chrysanthemum* plant named 'Yofiona', characterized by its compact, upright and somewhat outwardly spreading plant habit; freely branching habit; dense and full plant habit; uniform and freely flowering habit; medium decorative-type inflorescences with elongated oblong-shaped ray florets; coral bronze-colored ray florets; and natural season flowering in mid-September in the Northern Hemisphere.

2 Drawing Sheets

Botanical designation: *Chrysanthemum×morifolium.*
Cultivar denomination: 'Yofiona'.

BACKGROUND OF THE INVENTION

The present invention relates to a new and distinct cultivar of *Chrysanthemum* plant, botanically known as *Chrysanthemum×morifolium,* commercially known as a garden-type *Chrysanthemum* and hereinafter referred to by the name 'Yofiona'.

The new cultivar is a product of a planned breeding program conducted by the Inventor in Salinas, Calif. and Alva, Fla. The objective of the breeding program is to create new garden-type *Chrysanthemum* cultivars having inflorescences with desirable inflorescence forms, attractive floret colors and good garden performance.

The new *Chrysanthemum* originated from a cross-pollination made in December, 1999 in Salinas, Calif., of the *Chrysanthemum×morifolium* cultivar Yogretchen, disclosed in U.S. Plant Pat. No. 13,672, as the female, or seed, parent with a proprietary selection of *Chrysanthemum×morifolium* identified as code number 96-L011, not patented, as the male, or pollen, parent. The new *Chrysanthemum* was discovered and selected by the Inventor as a single flowering plant within the progeny of the stated cross-pollination grown in a controlled environment in Alva, Fla. in October, 2002. The selection of this plant was based on its desirable inflorescence form, attractive floret coloration and good garden performance.

Asexual reproduction of the new cultivar by terminal vegetative cuttings in a controlled environment in Alva, Fla. since January, 2003, has shown that the unique features of this new *Chrysanthemum* are stable and reproduced true to type in successive generations.

SUMMARY OF THE INVENTION

The cultivar Yofiona has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yofiana'. These characteristics in combination distinguish 'Yofiona' as a new and distinct cultivar:

1. Upright and somewhat outwardly spreading plant habit.
2. Freely branching habit; dense and full plants.
3. Uniform and freely flowering habit.
4. Medium decorative-type inflorescences with elongated oblong-shaped ray florets.
5. Coral bronze-colored ray florets.
6. Natural season flowering in mid-September in the Northern Hemisphere.

In side-by-side comparisons conducted in Alva, Fla., plants of the new *Chrysanthemum* differed from plants of the female parent, the cultivar Yogretchen, primarily in ray floret coloration as plants of the cultivar Yogretchen had orange-colored ray florets.

In side-by-side comparisons conducted in Alva, Fla., plants of the new *Chrysanthemum* differed from plants of the male parent selection in the following characteristics:

1. Plants of the new *Chrysanthemum* were fuller and more mounded than plants of the male parent selection.
2. Plants of the new *Chrysanthemum* flowered more uniformly than plants of the male parent selection.
3. Plants of the new *Chrysanthemum* had smaller inflorescences than plants of the male parent selection.
4. Ray florets of plants of the new *Chrysanthemum* were more bronze/less purple in color than ray florets of plants of the male parent selection.
5. Plants of the new *Chrysanthemum* had fewer disc florets per inflorescence than plants of the male parent selection.
6. Plants of the new *Chrysanthemum* flowered about six days earlier than plants of the male parent selection when grown under natural season conditions.

Plants of the new *Chrysanthemum* can be compared to plants of the *Chrysanthemum* cultivar Dark Grenadine, disclosed in U.S. Plant Pat. No. 7,632. In side-by-side comparisons conducted in Alva, Fla., plants of the new *Chrysanthemum* differed from plants of the cultivar Dark Grenadine in the following characteristics:

1. Plants of the new *Chrysanthemum* were smaller and more mounded than plants of the cultivar Dark Grenadine.
2. Plants of the new *Chrysanthemum* had smaller inflorescences than plants of the cultivar Dark Grenadine.
3. Plants of the new *Chrysanthemum* were not susceptible to heat delay whereas plants of the cultivar Dark Grenadine were susceptible to heat delay.

Plants of the new *Chrysanthemum* can also be compared to plants of the *Chrysanthemum* cultivar Tuscany, not patented. In side-by-side comparisons conducted in Alva, Fla., plants of the new *Chrysanthemum* differed from plants of the cultivar Tuscany in the following characteristics:

1. Plants of the new *Chrysanthemum* were more mounded than and not as rounded as plants of the cultivar Tuscany.
2. Plants of the *Chrysanthemum* had better garden performance and were durable than plants of the cultivar Tuscany.
3. Plants of the new *Chrysanthemum* had smaller inflorescences than plants of the cultivar Tuscany.
4. Ray florets of plants of the new *Chrysanthemum* were more bronze/less pinkish coral in color than ray florets of plants of the cultivar Tuscany.
5. Ray florets of plants of the new *Chrysanthemum* had much better color retention than ray florets of plants of the cultivar Tuscany.
6. Plants of the new *Chrysanthemum* were not affected by heat delay whereas plants of the cultivar Tuscany were extremely affected by heat delay.

BRIEF DESCRIPTION OF THE PHOTOGRAPHS

The accompanying photographs illustrate the overall appearance of the new *Chrysanthemum*. These photographs show the colors as true as it is reasonably possible to obtain in colored reproductions of this type. Colors in the photographs may differ slightly from the color values cited in the detailed botanical description which accurately describe the colors of the new *Chrysanthemum*.

The photograph on the first sheet comprises a side perspective view of a typical flowering plant of 'Yofiona' grown in a container.

The photograph on the second sheet comprises a close-up view of typical inflorescences of the cultivar 'Yofiona'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in Leamington, Ontario, Canada during the summer in a glass-covered greenhouse and under conditions and practices which approximate those generally used in commercial garden-type *Chrysanthemum* production. Rooted cuttings were planted in 15.25-cm containers, grown under artificial long day conditions (four-hour night interruption) and pinched about ten days later. About ten days after the pinch, plants were then exposed to artificial short day conditions (11.5 hours light) until flowering. During the production of the plants, temperatures ranged from 18° C. to 38° C. Measurements and numerical values represent averages for typical flowering plants.

Botanical classification: *Chrysanthemum×morifolium* cultivar Yofiana.

Commercial classification: Decorative-type garden *Chrysanthemum*.

Parentage:

*Female, or seed, parent.*—*Chrysanthemum×morifolium* cultivar Yogretchen, disclosed in U.S. Plant Pat. No. 13,672.

*Male, or pollen, parent.*—Proprietary selection of *Chrysanthemum×morifolium* identified as code number 96-L011, not patented.

Propagation:

*Type.*—Terminal vegetative cuttings.

*Time to initiate roots.*—About four days at 21° C.

*Time to produce a rooted cutting.*—About ten to twelve days at 21° C.

*Root description.*—Fine, fibrous; white in color.

*Rooting habit.*—Freely branching.

Plant description:

*Plant form/growth habit.*—Perennial herbaceous decorative-type garden *Chrysanthemum*. Inverted triangle with mounded crown. Stems initially upright, then somewhat outwardly spreading; rounded growth habit. Freely branching with about nine primary branches with secondary lateral branches potentially forming at every node. Moderately vigorous to vigorous.

*Plant height.*—About 20 cm.

*Plant diameter.*—About 29 cm.

*Lateral branches.*—Length: About 16 cm. Diameter: About 5.5 mm. Internode length: About 1.1 cm. Aspect: Upright and somewhat outwardly spreading. Texture: Pubescent. Color: 146A.

*Foliage description.*—Leaf arrangement: Alternate. Length: About 5.2 cm. Width: About 3.75 cm. Apex: Cuspidate. Base: Mostly truncate. Margin: Palmately lobed, sinuses parallel to convergent. Texture, upper surface: Slightly pubescent. Texture, lower surface: Pubescent; veins prominent. Color: Developing and fully expanded foliage, upper surface: More green than 147A. Developing and fully expanded foliage, lower surface: Close to 147B. Venation, upper surface: More green than 147A. Venation, lower surface: Close to 147B. Petiole length: About 1.3 cm. Petiole diameter: About 3.5 mm. Petiole color, upper surface: Close to 146A. Petiole color, lower surface: Close to 146B.

Inflorescence description:

*Appearance.*—Decorative-type inflorescence form with elongated oblong-shaped ray florets. Inflorescences borne on terminals above foliage, arising from leaf axils. Ray florets developing acropetally on a capitulum. Above five inflorescences per secondary lateral branch.

*Flowering response.*—Under natural season conditions, plants flower in mid-September in the Northern Hemisphere.

*Inflorescence bud (before showing color).*—Height: About 4 mm. Diameter: About 6 mm. Shape: Oblate.

Color (lower surface of phyllaries): Close to 146A to more green than 147A.

*Inflorescence size.*—Diameter: About 3.4 cm. Depth (height): About 1.25 cm. Disc diameter: About 6 mm. Receptacle diameter: About 6 mm.

*Ray florets.*—Shape: Elongated oblong-shaped. Length: About 1.6 cm. Width: About 5 mm. Corolla tube length: About 4 mm. Corolla tube diameter: About 1 mm. Apex: Emarginate, rounded or acute. Margin: Fused. Texture, upper and lower surfaces: Smooth, glabrous; satiny. Orientation: Initially upright, then eventually perpendicular to the peduncle. Number of ray florets per inflorescence: About 150 in numerous whorls. Color: When opening and fully opened, upper surface: Close to 6A overlain with close to 46A to 53A; color becoming lighter with development. When opening and fully opened, lower surface: Close to 6C underlain with close to 53A to 59A.

*Disc florets.*—Shape: Tubular, elongated. Length: About 4 mm. Width, apex: About 1 mm. Width, base: About 1 mm. Number of disc florets per inflorescence: About 32. Color: Immature: Close to 9A. Mature: Apex: Close to 9A. Mid-section: Close to 154D. Base: Close to 155D.

*Phyllaries.*—Quantity per inflorescence: About 20. Length: About 5 mm. Width: About 2.5 mm. Shape: Ligulate. Apex: Acute. Base: Truncate. Margin: Entire. Texture, upper surface: Smooth, waxy. Texture, lower surface: Pubescent. Color, upper surface: Close to 146A. Color, lower surface: Close to 146A to more green than 147A.

*Peduncle.*—Length: First peduncle: About 2.5 cm. Fourth peduncle: About 3.1 cm. Diameter: About 2 mm. Strength: Strong. Aspect: About 40° from vertical. Texture: Pubescent. Color: Close to 146A.

*Reproductive organs.*—Androecium: Present on disc florets only. Anther length: Less than 1 mm. Anther color: Close to 12A. Amount of pollen: None observed. Gynoecium: Present on both ray and disc florets. Style length: About 4 mm. Style color: Close to 154A. Stigma color: Close to 9A.

*Seed/fruit.*—Seed and fruit production has not been observed.

Disease/pest resistance: Plants of the new *Chrysanthemum* have not been shown to be resistant to pathogens and pests common to *Chrysanthemums.*

Garden performance: Plants of the new *Chrysanthemum* have been observed to be tolerant to rain, wind and temperatures ranging from 0° C. to more than 38° C.

It is claimed:

1. A new and distinct cultivar of *Chrysanthemum* plant named 'Yofiona', as illustrated and described.

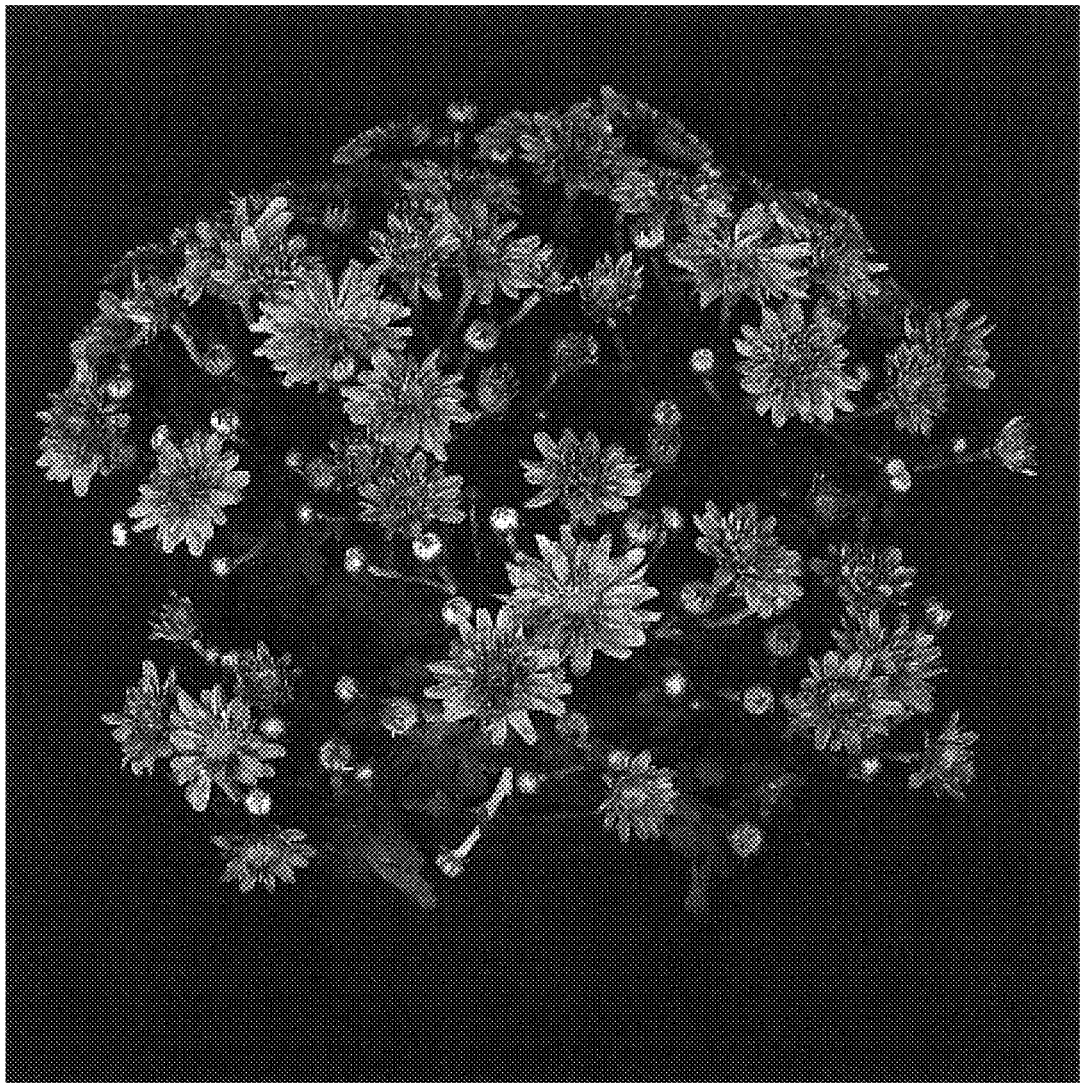

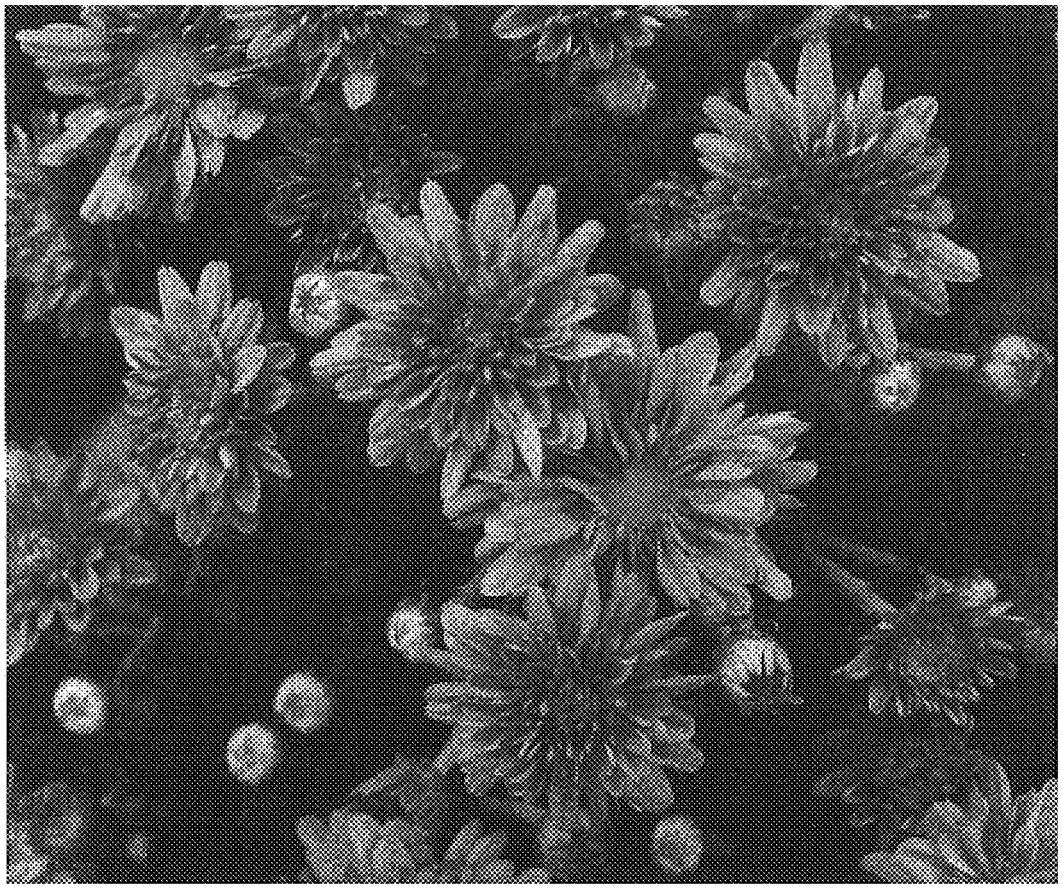

* * * * *